(12) United States Patent
Niedermeyer

(10) Patent No.: US 6,250,357 B1
(45) Date of Patent: *Jun. 26, 2001

(54) METHOD AND APPARATUS FOR BRIEFS WITH PAD SUPPORT PANEL

(76) Inventor: William P. Niedermeyer, 1024 Mt. Mary Dr., Green Bay, WI (US) 54311

( * ) Notice: Subject to any disclaimer, the term of this patent is extended or adjusted under 35 U.S.C. 154(b) by 0 days.

This patent is subject to a terminal disclaimer.

(21) Appl. No.: 09/268,220

(22) Filed: Mar. 15, 1999

(51) Int. Cl.$^7$ ..................................... B32B 31/00
(52) U.S. Cl. ................. 156/436; 156/465; 156/467; 156/516; 156/517; 156/519; 156/551; 156/160; 156/201; 156/204; 156/227; 156/256; 156/270; 156/300; 156/302
(58) Field of Search ........................... 156/256, 269, 156/270, 297, 299, 300, 302, 517, 519, 520, 160, 204, 201, 202, 227, 465, 467, 436, 516, 551

(56) References Cited

U.S. PATENT DOCUMENTS

| | | | |
|---|---|---|---|
| 4,578,133 | * | 3/1986 | Oshefsky et al. ............... 156/164 |
| 5,584,954 | * | 12/1996 | Van Der Klugt ............... 156/265 |
| 6,017,406 | * | 1/2000 | Vogt ........................... 156/73.1 |

* cited by examiner

*Primary Examiner*—Linda Gray

(57) ABSTRACT

The machine of the present invention fabricates an undergarment assembly having an elasticized pad support panel secured to inner surfaces of the rear panel and the openable front panel. The machine makes the garment assembly from two half width webs, one of which has a reinforced edge. The machine arrangement includes first and second transversely spaced web paths and components to bond tensioned elastic strands to spaced dots of adhesive located on a third pad supporting web that is secured to adhesive areas applied adjacent, but not in, the garment crotch area with spaced adhesive applied to the innermost surfaces of the rear and front panels. The machine includes devices to add side margin and front panel connecting tapes, and die cutting rolls to cut leg openings in side margins. The machine includes components to divert cull product and deliver flat unfolded product, or longitudinal and transverse folded products for packaging.

16 Claims, 4 Drawing Sheets

FIG. 11
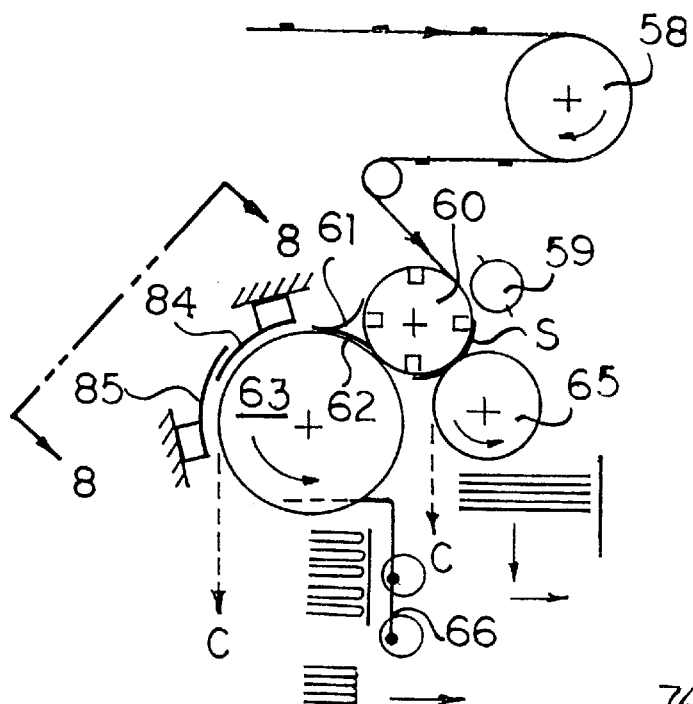
FIG. 12
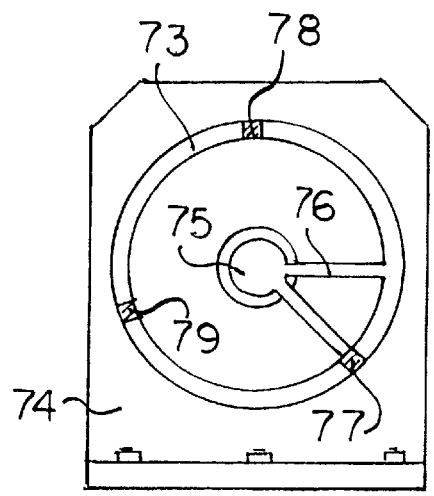
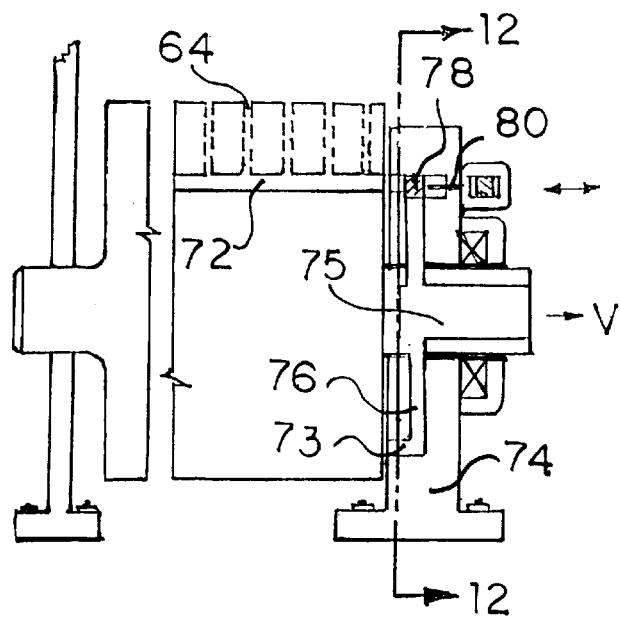
FIG. 13

METHOD AND APPARATUS FOR BRIEFS WITH PAD SUPPORT PANEL

BACKGROUND OF THE INVENTION

This invention relates to apparatus for fabricating undergarment assembly having a front opening, an integral inner pad support segment, and connecting tapes for completion of leg and waist apertures when the garment is applied to the wearer.

Apparatus of the instant invention fabricates a product similar to the undergarment assembly described in co-pending U.S. application Ser. No. 09/286355 including a combination of components to attach an elasticized pad support segment to the inside of the briefs.

The apparatus of this invention is a continuation-in-part of U.S. Pat. No. 5,904,802 with certain components eliminated and utilizes a different folding system to deliver stacks of flat unfolded product or stacks of longitudinally and transversely folded product for reduced package size.

The teaching of U.S. Pat. No. 5,904,802 produces a completed brief having leg and waist apertures. The brief is suitable for use by 'stepping into' the leg apertures.

The apparatus of the instant invention is arranged to make a product without waist and leg apertures completed and produces a product essentially intended to be applied like a disposable diaper while the wearer is in a prone or squatting position.

The instant invention includes apparatus for advancing, cutoff, and transfer of tape segments about 1" wide (longitudinal machine direction) or cover strip segments having a longitudinal dimension (machine direction) longer than about 6" using techniques described in U.S. Pat. No. 3,725,191 and other tape/segment advancing devices.

Speed ratios between web advancing rolls and the cutoff-transfer roll couples are changed to vary the length of the segments added by these devices.

The product made by the instant apparatus has two parallel stretched elastic strands (or pluralities thereof) added to the pad support segment before it is attached to the inside surface of the innermost segment of the brief according to U.S. Pat. No. 3,828,367 to Bourgeous, U.S. Pat. No. 4,081,301 to Buell.

After side tapes, front closure tape, and the pad support web are added, leg cutouts are made in side margins and the completed assembly is advanced to a cutoff, folding and transfer system for stack delivery.

Using transverse folding principles and apparatus according to U.S. Pat. No. 1,974,149 of Christman, (1934) or U.S. Pat. No. 3,400,641 to Stemmler, the product is folded for package size reduction without completion of leg and waist apertures and delivered in stacks for packaging.

SUMMARY OF THE INVENTION

It is an object of this invention to describe fabricating apparatus for producing a front opening undergarment assembly containing a pad support segment substantially equal in width to the overlapped central portion of the product, attached to, and suspended from, the front and rear panel portions of the product.

It is a further object of the invention to provide apparatus for attachment of elastic strands along opposite side margins of the support segment.

It is an object of the invention to define apparatus that delivers stacks of product without cross folds or stacks having transverse folds for package size reduction.

It is an further object of this invention to provide apparatus for making longitudinal folds to reduce width of the product for packaging.

It is a further object of this invention to describe apparatus that diverts faulty product as rejected cull.

Other objects of the invention will be seen in the ensuing specifications.

BRIEF DESCRIPTION OF THE DRAWINGS

FIG. 11 is a schematic side elevation of folding apparatus for delivery of flat product or stacks of folded product illustrating the devices for completing longitudinal folds.

FIG. 12 is a side elevation of the stationary half of a vacuum timing valve viewed from line 12—12 of FIG. 13.

FIG. 13 is a schematic side elevation illustrating a vacuum roll cooperatively arranged with the stationary half portion of a vacuum timing valve including a movable block for changing length of a vacuum channel.

DETAILED DESCRIPTION

Figure 1:
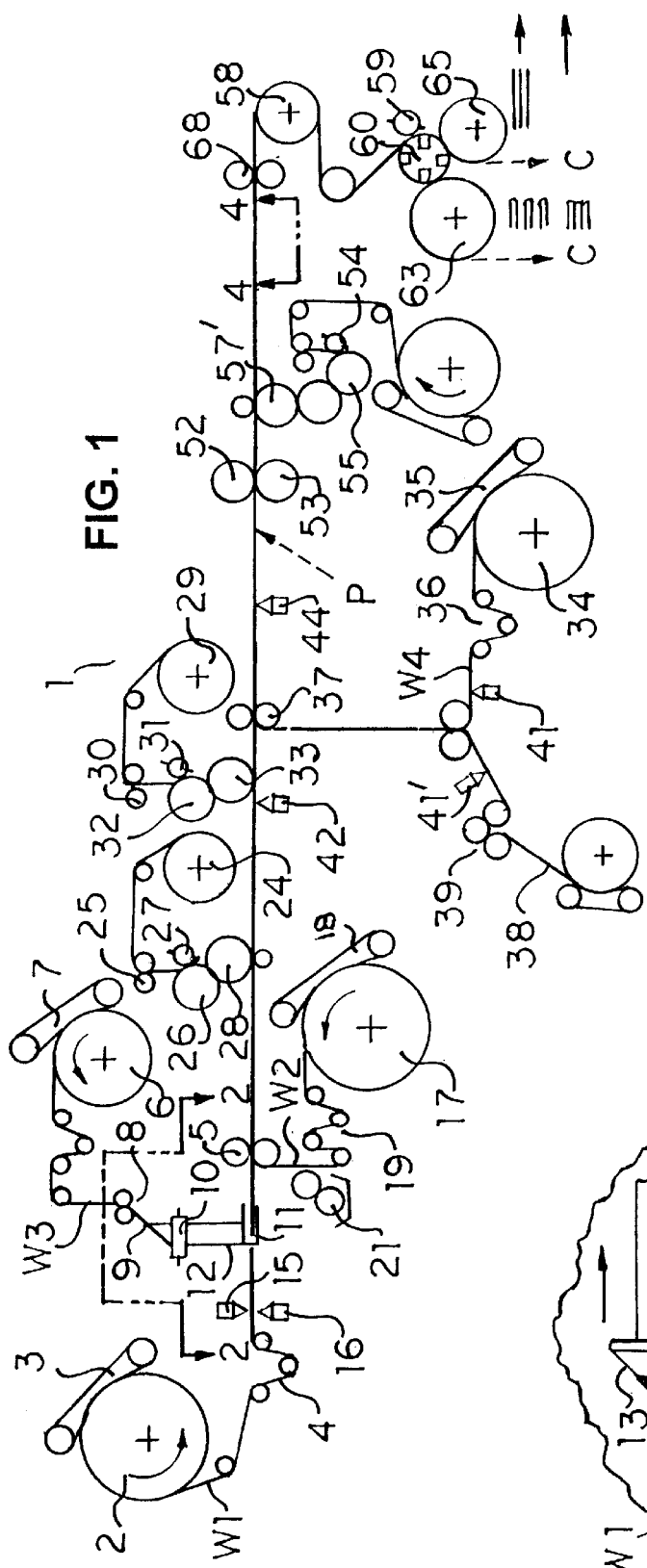
FIG. 1 is a side elevation schematic of the apparatus of the instant invention.
Figure 9:
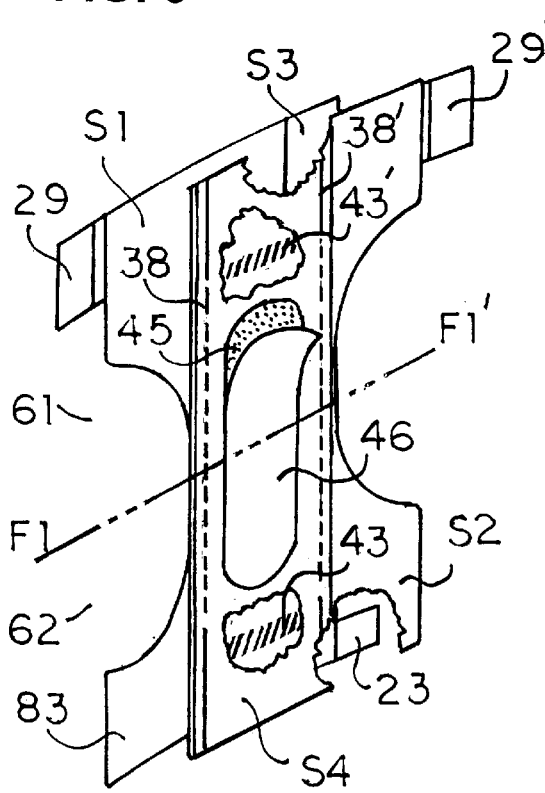
FIG. 9 is a perspective view of the product fabricated on the apparatus of FIG. 1 illustrating the pad support segment with an attached pad or removable cover strip.

In FIG. 1, manufacturing apparatus 1 substantially complates the undergarment assembly shown in FIG. 9 while materials are in web form, and delivers separated products in stacks of flat unfolded assemblies, or in another embodiment, in stacks of longitudinally and transversely folded product.

In FIG. 1, web W1 is unwound from supply roll 2 by unwind belt 3, and advances through 3-roll constant tension system 4.

Web W1 and W2 are referred to as first and second webs herein.

In FIG. 1, a narrow web strip W3 is unwound from supply roll 6 by unwind belt 7 and passes through the nip of pull roll pair 8 mounted above v-folding plate 9.

A second pair of draw rolls 10 at the tip of folding plate 9 is driven by a variable speed motor (not shown) to create tension in the web moving across folding plate 11. The apex of the v-folded web is along margin 12 (see FIG. 3).

Figure 2:
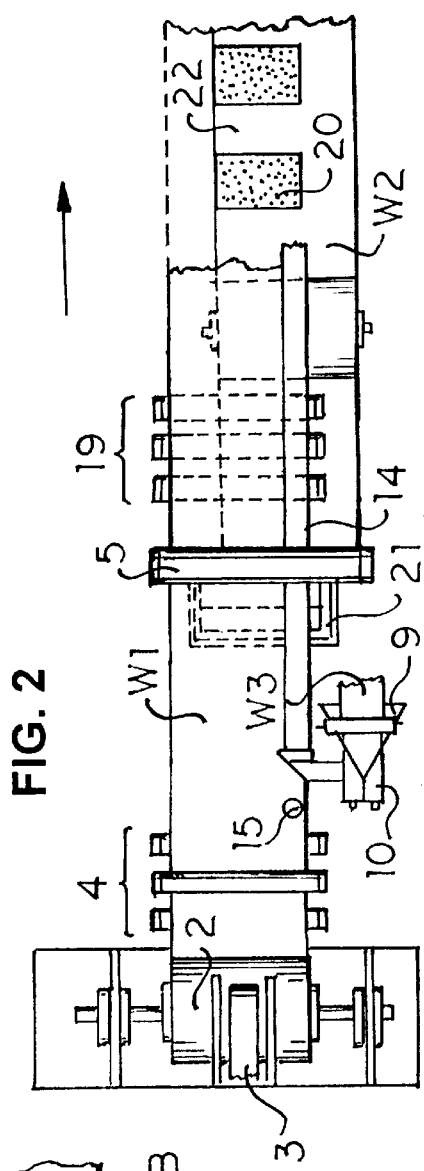
FIG. 2 is a top plan view of the web overlapping arrangement viewed from sightline 2—2 of FIG. 1.
Figure 3:
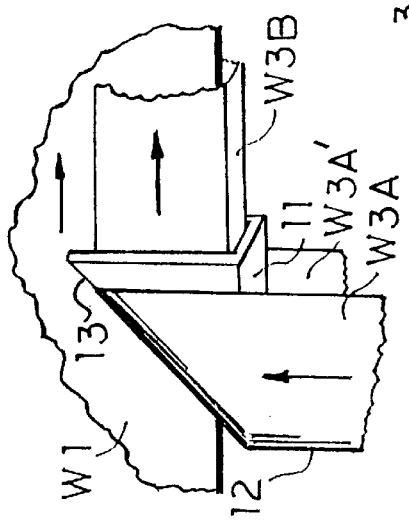
FIG. 3 is an enlarged fragmentary vew of the inverse folding plate pair for adding a reinforcing strip to the edge of one web.

Referring briefly to FIGS. 2 and 3, the V-folded web is advanced from pull rolls 10 over guide rolls (not shown) to the incoming web position W3A, advanced over the top and bottom outside surfaces of inverse folding plates 11, around the 45 degree angled edges 13, and is reverse folded to slide over the inside surfaces and exit from plate pair 11, with web W3B oriented 90 degrees from the direction of the incoming web—in effect, a 90 degree turn involving a reversal of inside and outside surfaces before and after the web fold.

The apex of the inversely folded web is along edge 14 after exit from plates 11.

Figure 5:
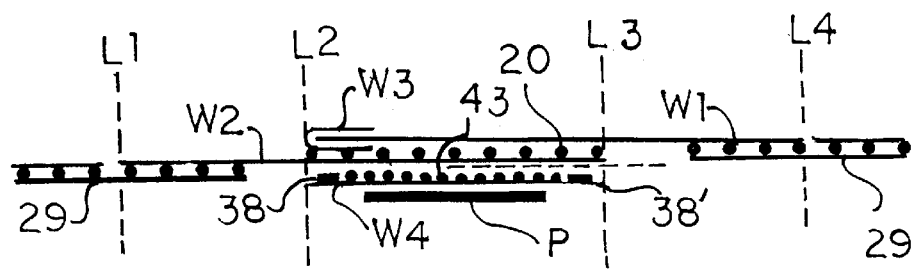
FIG. 5 is a cross sectional diagrammatic illustration of the assembly viewed from line 5—5 of FIG. 4.

In FIGS. 2 and 5, first web W1 is shown entering the space between the reverse portions of strip W3 and is enclosed therebetween.

In FIG. 2, the reinforcing strip W3 is attached to adhesive applied to both sides of web W1 by applicators 15 and 16 (not shown).

In FIG. 3, means to change spacing between upper and lower angled plates can be provided (not shown) to increase spacing when W1 or W3 spliced joints are sensed upstream, and can be reduced to normal spacing using automatic controls.

It is further noted that while strip reinforcing web W3 is shown being added to web W1, duplicate but oppositely handed means can be used to add a strip to the edge of web W2.

In FIG. 1, second web W2 is concurrently fed from supply roll 17 by unwind belt 18 and passes through a 3-roll constant tension system 19.

Before being joined to web W1, the underlying web W2 (see FIGS. 1 and 2) has adhesive applied to restricted spaced areas 20 in the central overlapped region by printer 21.

Spaced areas of adhesive 20 (see right side of FIG. 2) joins the two half width webs into a full width web at spaced intervals of the overlapped portions between plies of the rear panel, and by leaving a portion not adhesively printed (space 22 between areas 20—see right side of FIG. 20), the unbonded overlap becomes the front panel opening.

It is noted that when the longitudinal dimension of the printed area 20 exceeds 50% of the product length, a limited but beneficial bonding occurs between a portion of the overlapped front panel plies near the crotch.

In FIG. 1, web W2 is advanced to the nip between roll set 5 and bondably joined in spaced adhesive areas 20 to web W1 including reinfrocing strip W3 that encloses one margin.

Figure 4:
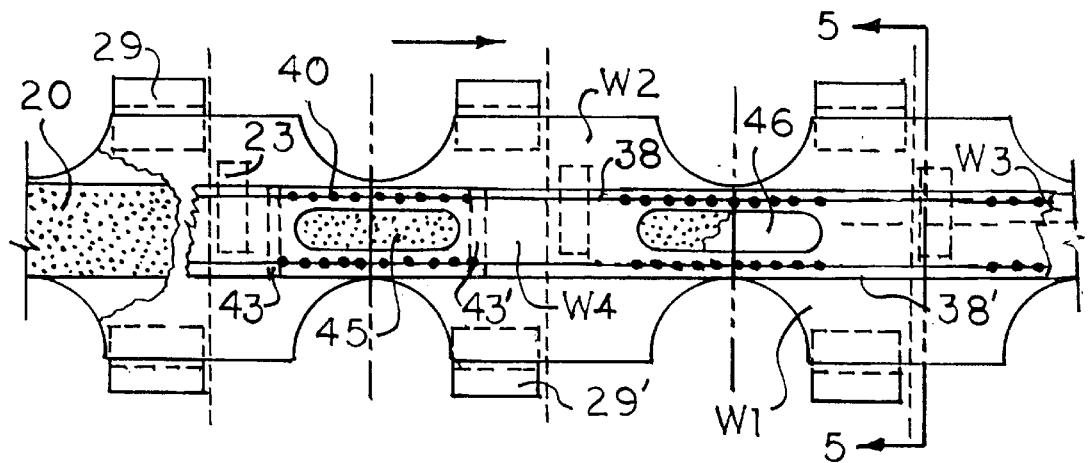
FIG. 4 is an illustration of the underside of the web assembly W1, W2, and W3 viewed from sight line 4—4 of FIG. 1 (see right side).

In FIGS. 2 and 4, the conjoined webs are viewed with web W1 overlapped as the top web.

In other embodiments, webs can be interchanged to yield an oppositely handed front panel opening.

Before reaching transverse cutting rolls, a releaseable closure tape 23 (see FIG. 9) is attached to the top of web W1 and extends over the folded edge of the reinforcing strip for attaching connection between the two half width webs which become the front panel when the garment is folded around the crotch of the wearer.

In the top of FIG. 1, a closure tape is pulled from supply roll 24 by draw rolls 25.

The web for tape 23 is flexible but substantially non-extensible.

With a disc brake or other means to provide resistance, the tape web being fed into roll set 25 has enough tension to prevent overfeed while advancing (for example, a 1" long segment) into the space between anvil roll 26 and knife roll 27 when the knife-anvils are not in contact between cuts.

Vacuumized anvil roll 26 advances the tape segment to vacuum transfer roll 28 for extending attachment to overlapped webs W1 and W2.

In FIG. 1, two webs 29, 29' of side margin tapes are advanced from a supply roll, threaded over a guide roll (not referenced) and around pull rolls 30 for segment advancement to cutoff roll set 31, 32 and vacuum transfer roll 33 in a segment feeding system similar to U.S. Pat. No. 3,728,191 and other prior art.

In the lower part of FIG. 1, web W4 (for pad support segment S4 see FIG. 9) is unwound from supply roll 34 by unwind belt 35.

Web W4 is advanced over a 3-roll constant tension system 36 by a set of pull rolls 37.

Elastic strands 38, 38' pass through the nip of S-wrap roll set 39 which advances the elastic at a velocity lower than the velocity of the pad support web W4, thus inducing tension in the elastic strands according to the teaching of U.S. Pat. No. 4,240,866.

Strands 38, 38' remain tensioned and stretched until the web assembly is cut into separate garments.

In FIG. 1, spaced portions of elastic strands 38, 38' are superposed on dots of adhesive 40 placed on web W4 at spaced intervals (see FIG. 4) by applicator 41. In another embodiment, adhesive can be applied to the elastic strands as at 41' in FIG. 1.

Upstream of pull rolls 37 in FIG. 1, adhesive applicator 42 applies spaced areas of adhesive 43, 43' to the underside of web W2.

Areas 43, 43' are spaced apart longitudinally at a distance substantially equal to, or slightly longer than, the longitudinal distance of the series of spaced dots applied to web W4.

By attachment of web W4 near opposite ends, the segment between attachment zones 43, 43' is therefore free to contract along with the attached tensioned elastic strands without affecting the length of the non-stretched undergarment material between areas of pad support attachment.

In FIG. 1, after tensioned elastic is applied to web W4 the web with elastic 38 is attached at spaced apart areas 43, 43' (see FIG. 4), adhesive applicator 44 applies pad receptor adhesive to areas 45 of FIG. 4.

If a pad is not added during fabrication of the assembly, receptor area adhesive 45 must be covered with a release coated strip 46 of FIG. 4 (means not shown in FIG. 1).

Figure 6:
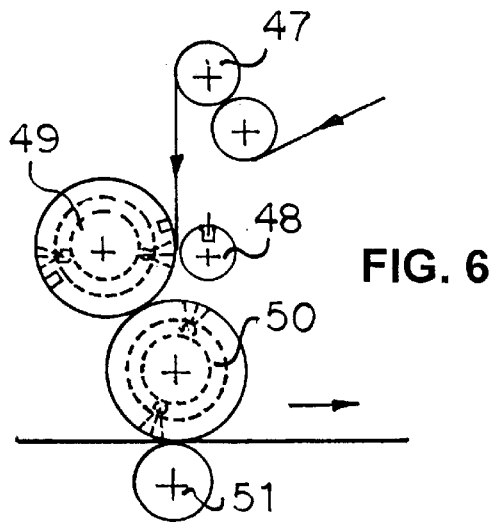
FIG. 6 is an enlarged side elevation schematic illustrating a web advance, cutoff and trasnsfer system for attachment of tapes and other segments to the top of a primary web.

In an embodiment requiring strip 46, a system similar to the segment (ot tape) feeder system of FIG. 6 is used as described hereinafter.

FIG. 4 is viewed from the underside of the overlapped webs W1 and W2 to show the pad support web W4 and its attachment to adhesive receptor areas 43, 43'.

Elastic strands 38, 38' are attached to the pad support and enclosed between bottom web W2 and pad support web W4 (see also FIG. 5)

In FIG. 5, web W1 extends between L2 to L4, and web W2 extends from L1 to L3 for bonded attachment by adhesive 20.

In FIG. 5, web W4 extends from L2 to L3 and is attached to the underside of the overlapped webs with adhesive applied in areas 43, 43'.

In FIG. 5, a separate pad P is shown, but pad receptor adhesive is omitted for clarity.

Figure 7:
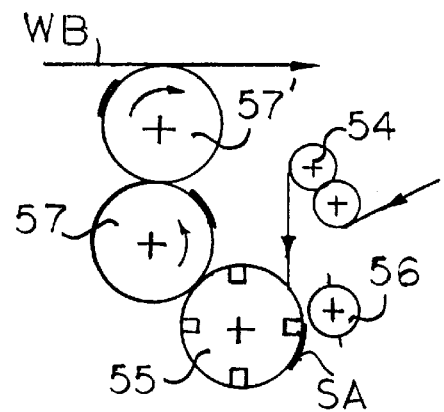
FIG. 7 is a side elevation schematic of a system for advancement, cutoff, and transfer of a segment for attachment to the underside of a primary web.

FIGS. 6 and 7 are typical segment feeder devices with similar components but with different arrangements depending on the direction of the incoming web and final transfer to the top or bottom of the primary web.

FIG. 6 is an enlarged view of the segment feed system for adding front closure tapes 23 and side tapes 29, 29' (see FIG. 9).

In FIG. 6, an S-wrap feed roll couple 47 advances a web at slow speed to advance a portion that protrudes downwardly in the space between knife cutoff roll 48 and anvil roll 49.

During the interval betqween cuts, the advancing segment is in sliding contact with anvil roll 49 which has vacuum ports at small segment repeats, and when the cutoff roll rotates to the cutting position, a small segment (such as a tape) is free to advance at web speed on the surface of roll 49 for transfer to the web via roll 50. A backup roll 51 is provided for web support.

Referring briefly to FIG. 1, die roll 52 coacting with anvil roll 53 is shown immediately downstream of applicator 44 and position P. The die set cuts excess material from side margins to form an hourglass shape for leg apertures.

FIG. 7 is an enlarged view of a similar feed, cutoff, and transfer system used to add a cover strip 46 over receptor area 45 (see FIG. 4).

S-wrap roll set 54 directs the leading edge of a web to the surface of anvil roll 55. Web W A is restrained by roll set 54 and held in sliding contact with roll 55 by vacuum ports in the surface of roll 55 until the cutoff occurs.

By using well known rotary vacuum valves (see FIGS. 12 and 13) a cut segment S is transferred to web W B via rolls 57, 57'.

Referring to FIG. 1 and 11, web assembly W 1, W 2, W 3, and W 4 is advanced around reversing roll 58 to place tapes on the underside of the advancing web assembly.

Knife roll 59 severs the web assembly into segments S. Anvil roll 60 is vacuumized and advances the leading cut edge to anvil roll position at about 290 degrees (as viewed in FIG. 11).

The leading rear panel 61 (see also FIG. 9) is held to anvil roll 60 until vacuum is stopped at about 285 degrees.

Figure 8:
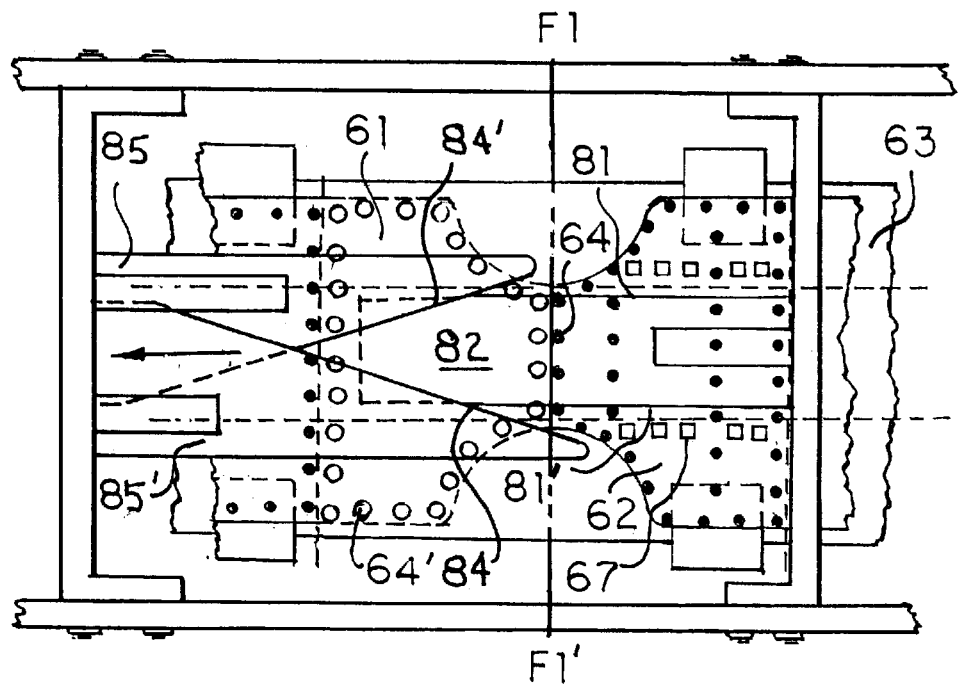
FIG. 8 is a plan view of the product on the surface of a folding roll illustrating the use of cooperating plate edges and inclined folding plates to complete longitudinal folds. Curvature of elements is omitted for clarity.

In FIG. 11, the trailing front panel portion 62 (see FIG. 9) is held by vacuumized apertures shown solid in FIG. 8, and as folding roll 63 rotates, a plurality of vacuum ports 64 along fold line F1–F1' holds the trailing panel 62 near the fold line and causes rear panel 61 to be slideably pulled from the surface of roll 60, resulting in a half fold to reduce packaging size.

In FIG. 8, vacuum ports for rear panel 61 are shown as circles and ports for front panel 62 are shown solid, noting that the same pattern of ports are on rolls 60,63, and 65.

Some of the ports for leading panel 61 are omitted for clarity.

Attention is directed to square ports 67 (see FIG. 8) in the surface of rolls 60, 63, and 65.

Air pressure is applied through apertures 67 to eject faulty product from rolls 62, 65 of FIG. 11 or delivery roll 65 of FIG. 10, but more importantly, to provide a first positive upward force to fold outer side panel 'wing' portions of the garment radially outward from roll 63 of FIG. 11 as described hereinafter for making longitudinal folds.

Figure 10:
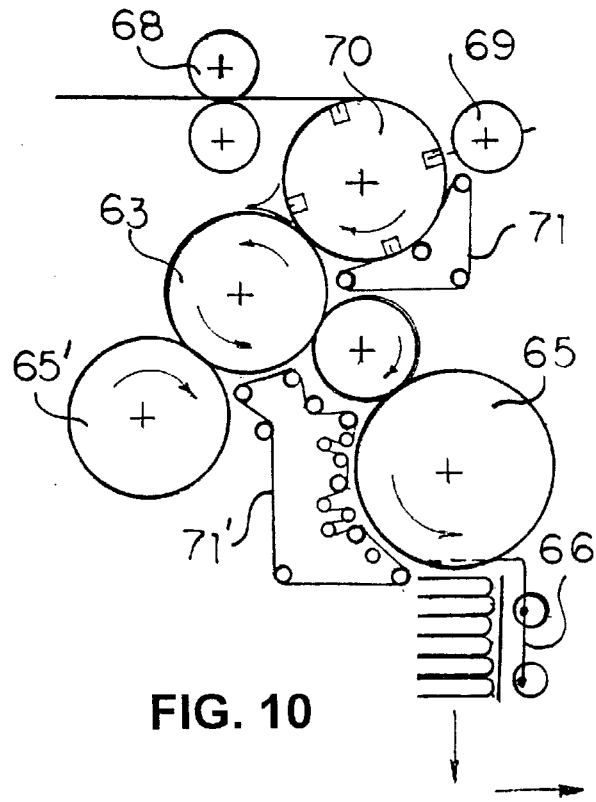
FIG. 10 is a schematic side elevation of folding apparatus illustrating a coacting containment belt system.

The cutting, folding and transfer arrangement of FIG. 10 has components similar to FIG. 11 including nip rolls 68 to isolate elastic tension in the product during the cutting operation between knife roll 69 and anvil roll 70. Product control belts 71, 71' keep product against roll surfaces.

FIG. 13 shows a typical plurality of ports 64, 64' (see FIG. 8) communicating with vacuum manifold 72 in a typ[ical rotating roll.

The circular free end of manifold 72 rotates in sliding contact with annular groove 73 in stationary valve half 74, (viewed from sight line 12—12 of FIG. 13).

Annular groove 73 communicates with central hollow shaft 75 via radial channels 76.

For example, in FIG. 12, vacuum V is only available in the groove between positions 77 to 78 and 78 to 79.

Referring to FIG. 13, the crosshatched block in position 78 is connected to, and slideable with, solenoid actuator rod 80, and by slideable retraction into block cutouts in the frame (not referenced for clarity), block 78 can be moved to restore the full vacuum path between 77 and 79.

In FIGS. 12 and 13, the solenoid actuator causes a change in duration of the effective vacuum by interruption of the vacuum path 77–79 resulting in longer or shorter groove length and different vacuum duration which is used to reject defective product along paths C in FIGS. 10 and 11.

Referring back to FIG. 8, central folding edges 81, 81' of plate 82 provide a folding edge around which panels extending transversely beyond the crotch (see 83 of FIG. 9) are folded by applying air pressure through square apertures 67 to force wing portions 83 to be folded upwardly, and during subsequent advancement, to be folded inwardly in superposed relationship by folding edges 84, 84' of plates 85, 85' respectively.

It is further understood that the present invention may be embodied in other specific forms without departing from the spirit or special attributes, and it is, therefore, not restrictive, reference being made to the appended claims rather than to the foregoing description to indicaste the scope of the invention.

Having thus described the invention, what is claimed as new ans desired to protect by Letters Patent are the following:

1. Apparatus for fabricating an undergarment assembly having an inner pad support member superposed on and attached to spaced areas of a unitary rear panel portion and to a front panel portion having a reclosable opening, said apparatus including:

means to position first and second web supply rolls on transversely spaced centerlines, said first and second webs each having a width substantially equal to one half the product width plus an amount for overlap, means to advance said first web along a first path, means to advance said second web along a second path, a first means to apply bonding agent to a longitudinally spaced area on at least one of said webs, said area facing the other of said webs, means to partially superpose said second web and said first web in partially overlapped relationship along a conjoined path to form an assembly having innermost and outermost webs, means to bond spaced apart overlapped areas of said first web to said second web, said spaced bonded areas forming the unitary rear panel, means to advance, cut, and attach pairs of tapes, each having a portion extending from opposite sides of the undergarment assembly, means to advance, cut, and apply a release coated cover strip to each of said extending tape portions, said cover strips for removal by user before said extending tape portions are manually folded over to connect said rear panel to said front panel, means for attaching a portion of a closure tape to the first half width web, said closure tape extending beyond the overlapped margin of said first web and protruding over said second half width web for attachment of said frist and second half width webs to form the connected front panel portion of said undergarment assembly, means to cut curvilinear leg opening portions along non-overlapped side margins of said conjoined first and second web asssemby, a second means to apply adhesive to spaced receptor areas on the inner surface of the innermost half width web, means to apply spaced dots of adhesive on at least two tensioned elastic strands and bonding the tensioned strands along margins of a third support panel web, means to advance and bondably attach the third support panel web to said spaced adhesive receptor areas on said innermost half width web, means to cut said bonded rear panel and connected front panel into the undergarment assembly, means to remove said undergarment assembly from said conjoined path.

2. The apparatus of claim 1 including means to apply adhesive to a pad receptor area on the inside surface of the third support web.

3. The apparatus of claim 2 including means to advance, cutoff, and superpose a release coated strip to said pad receptor area on the third web.

4. The apparatus of claim 2 including means to advance and bondably attach an absorbent pad to said pad receptor area on the third web.

5. The apparatus of claim 1 wherein said segment path removal means includes a roll having a plurality of vacuum ports along a transverse line that bisects said leg openings.

6. The apparatus of claim 1 including means to advance an additional web, fold said additional web longitudinally, change advancement direction, fold said additional web to reverse inside and outside surfaces, and enclose at least one of said first and second web along one edge within said additional web.

7. The apparatus of claim 1 wherein said means to advance said second web is arranged to partially superpose said second web on top of said first web.

8. The apparatus of claim 1 wherein means to apply said front panel connection tape includes means to apply a tape protrusion to a release coated receptor area of one of said other half width web.

9. The apparatus of claim 1 wherein said segment path removal means includes the means to cut leg openings before removel from said path.

10. The apparatus of claim 1 wherein said leg opening cutting means is arranged in timed relationship with said web assembly to cut said leg openings symmetrically about a line substantially midway between end margins of said cut undergarment assembly.

11. The apparatus of claim 1 wherein said segment assembly path removal means is a vacuumized transfer roll.

12. The apparatus of claim 1 wherein said path removal means is a vacuumized transfer roll in folding cooperation with a roll having at least one anvil, the transfer roll being substantially flush with the surface of said anvil roll and arranged parallel with the axis of rotation of the anvil.

13. The apparatus of claim 1 wherein said segment path removal means includes electronically actuated means to change duration of vacuum applied to said path removal means.

14. The apparatus of claim 1 wherein said segment path removal means includes cooperating endless belts in contacting realtionship with a segment held against a surface of said path removal means.

15. The apparatus of claim 1 including means to longitudinally fold a side margin on each of said first and second webs after said leg opening cutting means.

16. A method of fabricasting an undergarment assembly having a front opening and an inner pad support segment with elasticized side margins including the steps of:

providing a first web and a second web each having a width substantially equal to half the undergarment width, advancing said first web along a first path advancing said second web along a second path transversely offset from said first path, applying a bonding agent to longitudinally spaced areas of one of the webs, said areas facing the other of said webs, superposing said first and second webs in partially overlapping relationship to form an assembly having innermost and outermost webs, joining said first and second webs and bonding said webs in said longitudinally spaced areas along a conjoined path to form a unitary rear panel, cutting, advancing, and attaching at least one pair of tapes, each having a portion protruding from opposite side margins of the undergarment assembly, advancing, cutting, an applying a release coated cover strip to tape portions protruding from each of said side margins, attaching a connecting tape over an overlapped margin of one of the webs and securing a protruding end of said tape to the other of said webs to form a connected assembly having a non-bonded front panel opening, cutting curvilinear leg opening portion from non-overlapped side margin of the assembled webs, applying adhesive to longitudinally spaced receptor areas on the inner surface of the innermost web, applying spaced dots of adhesive on at least two tensioned elastic strands and bonding the strands along margins of a third support panel web, advancing and bondably attaching the third web to said spaced adhesive receptor areas on the inner surface of the assembled webs, severing said joined and connected half width webs into the undergarment assembly, removing the undergarment assembly from said conjoined path.

* * * * *